United States Patent
Barnes et al.

(10) Patent No.: US 11,105,732 B2
(45) Date of Patent: Aug. 31, 2021

(54) APPARATUS AND METHOD FOR MEASURING WET FRICTION OF HAIR

(71) Applicant: Conopco, Inc., Englewood Cliffs, NJ (US)

(72) Inventors: Andrew Anthony Howard Barnes, Port Sunlight (GB); Fraser Ian Bell, Higher Bebington (GB); Colin Christopher David Giles, Oxton (GB); Sophia Paraskevi Clare Moghadam, Bromborough (GB); Rongrong Zhou, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 155 days.

(21) Appl. No.: 16/497,300

(22) PCT Filed: Mar. 21, 2018

(86) PCT No.: PCT/EP2018/057202
§ 371 (c)(1),
(2) Date: Sep. 24, 2019

(87) PCT Pub. No.: WO2018/177849
PCT Pub. Date: Oct. 4, 2018

(65) Prior Publication Data
US 2021/0123856 A1    Apr. 29, 2021

(30) Foreign Application Priority Data
Mar. 29, 2017   (EP) ..................... 17163597

(51) Int. Cl.
*G01N 19/02*   (2006.01)
*G01N 33/483*  (2006.01)
*A61K 8/41*    (2006.01)

(52) U.S. Cl.
CPC .............. *G01N 19/02* (2013.01); *A61K 8/416* (2013.01); *G01N 33/4833* (2013.01)

(58) Field of Classification Search
CPC ....................................................... G01N 19/02
(Continued)

(56) References Cited

U.S. PATENT DOCUMENTS 2,712,235 A  *  7/1955  Harlan ................... G01N 33/32
                                                73/150 R
3,161,704 A  * 12/1964  Le Grand ................ G01B 7/34
                                                 264/40.1
(Continued)

FOREIGN PATENT DOCUMENTS

EP    0965834    12/1999
EP    1652555     5/2006
(Continued)

OTHER PUBLICATIONS

Yuuki Aita et al., "Friction and Surface Temperature of Wet Hair Containing Water, Oil, or Oil-in-Water Emulsion", Journal of Oleo Science, No. 65, 2016. (Year: 2016).*

(Continued)

*Primary Examiner* — David A. Rogers
(74) *Attorney, Agent, or Firm* — Gerard J. McGowan, Jr.

(57) ABSTRACT

A system for the measurement of wet friction of a bundle of hair fibres includes a friction probe, a means for securing a bundle of hair fibres, and a water bath. The friction probe includes a contact surface. The friction probe is fitted with a weight in the range of from 10 g to 500 g, inclusive. The friction probe is connected to a texture analyser. The means and the friction probe are positioned in the water bath below a fill line. The contact surface of the friction probe comprises surfactant.

13 Claims, 3 Drawing Sheets

(58) Field of Classification Search
USPC .................................................................. 73/9
See application file for complete search history.

(56) References Cited

U.S. PATENT DOCUMENTS

| | | | | |
|---|---|---|---|---|
| 3,717,025 | A * | 2/1973 | Kronenberg | G01N 19/02 73/9 |
| 3,721,250 | A * | 3/1973 | Walter | A45D 20/50 132/112 |
| 3,921,443 | A * | 11/1975 | Yates | G01N 3/066 73/817 |
| 3,946,606 | A * | 3/1976 | Abrioux | G01L 1/044 73/160 |
| 3,960,160 | A * | 6/1976 | Hogan | A45D 24/22 132/112 |
| 4,061,022 | A * | 12/1977 | Yates | G01N 3/08 73/764 |
| 4,167,869 | A * | 9/1979 | Gikas | A45D 24/10 132/219 |
| 4,286,469 | A * | 9/1981 | Trias | G01N 3/08 73/829 |
| 4,722,218 | A * | 2/1988 | Strader | G01N 19/02 73/9 |
| 5,358,667 | A * | 10/1994 | Bergmann | A61K 8/345 510/122 |
| 5,373,723 | A * | 12/1994 | Chou | G01N 19/02 271/263 |
| 5,767,104 | A * | 6/1998 | Bar-Shalom | A61K 8/02 514/23 |
| 6,234,003 | B1 | 5/2001 | Nakajima | F16J 15/3296 73/9 |
| 6,321,586 | B1 * | 11/2001 | Wojtowicz | G01N 3/56 73/9 |
| 6,494,076 | B1 * | 12/2002 | Gent | G01N 19/02 73/9 |
| 6,817,222 | B2 * | 11/2004 | Day | G01N 19/02 73/9 |
| 8,833,137 | B2 * | 9/2014 | Yagnik | A61K 8/463 73/9 |
| 9,823,180 | B2 * | 11/2017 | Amano | G01N 19/02 |
| 9,829,419 | B2 * | 11/2017 | Fawcett | G01N 1/28 |
| 10,024,841 | B2 * | 7/2018 | Meinert | G01N 19/02 |
| 10,151,684 | B2 * | 12/2018 | Ganguli | G01N 19/02 |
| 10,809,181 | B2 * | 10/2020 | Justynska-Reimann | G01N 19/02 |
| 2003/0140707 | A1 | 7/2003 | Pyle et al. | |
| 2003/0233861 | A1 * | 12/2003 | Woolston | G01N 19/02 73/9 |
| 2005/0112074 | A1 | 5/2005 | Arai et al. | |
| 2006/0184068 | A1 * | 8/2006 | Shibuichi | G01N 19/02 600/587 |
| 2007/0288186 | A1 | 12/2007 | Datta et al. | |
| 2008/0233069 | A1 * | 9/2008 | Tamareselvy | C08F 293/005 424/70.11 |
| 2009/0031791 | A1 * | 2/2009 | Zahouani | A61B 5/441 73/105 |
| 2009/0071228 | A1 | 3/2009 | Sherman et al. | |
| 2009/0188330 | A1 * | 7/2009 | Kindersley | G01N 19/02 73/862.21 |
| 2009/0324529 | A1 | 12/2009 | Okada et al. | |
| 2009/0324532 | A1 | 12/2009 | Okada et al. | |
| 2010/0223977 | A1 * | 9/2010 | Debon | G01N 33/04 73/9 |
| 2012/0222466 | A1 * | 9/2012 | Bailey | A61B 5/1072 73/9 |
| 2014/0311210 | A1 * | 10/2014 | Rounds | G01N 19/02 73/9 |
| 2015/0241332 | A1 * | 8/2015 | Amano | G01N 3/08 73/9 |
| 2015/0292989 | A1 | 10/2015 | Regimand et al. | |
| 2015/0355063 | A1 * | 12/2015 | Fawcett | G01N 1/28 73/829 |
| 2016/0061809 | A1 * | 3/2016 | Meinert | G01N 33/483 73/159 |
| 2016/0279048 | A1 * | 9/2016 | Jayaswal | A61Q 5/02 |
| 2017/0138839 | A1 * | 5/2017 | Ganguli | G01N 19/02 |
| 2017/0231897 | A1 * | 8/2017 | Avery | A61Q 5/12 424/70.122 |
| 2017/0266099 | A1 * | 9/2017 | Kroon | C08F 222/38 |
| 2018/0177696 | A1 * | 6/2018 | Schrott | A61K 8/345 |
| 2018/0221266 | A1 * | 8/2018 | Zhao | A61K 8/35 |
| 2018/0345048 | A1 * | 12/2018 | Dussaud | A61K 8/27 |
| 2018/0353396 | A1 * | 12/2018 | Paul | A61K 8/86 |
| 2018/0353398 | A1 * | 12/2018 | Torres Rivera | A61K 8/35 |
| 2019/0192405 | A1 * | 6/2019 | Zhao | A61K 8/046 |
| 2019/0293548 | A1 * | 9/2019 | Krishan | A45D 24/10 |
| 2020/0197273 | A1 * | 6/2020 | Coan | A61K 8/416 |
| 2020/0217779 | A1 * | 7/2020 | Brada | G01N 33/4833 |
| 2020/0330351 | A1 * | 10/2020 | Kong | A61K 8/365 |

FOREIGN PATENT DOCUMENTS

| | | | | |
|---|---|---|---|---|
| EP | 3287119 | A1 * | 2/2018 | A61K 8/45 |
| JP | 57166545 | A * | 10/1982 | G01N 3/58 |
| JP | 62273433 | A * | 11/1987 | |
| WO | WO-91/15763 | | * 10/1991 | |
| WO | WO0224071 | | 3/2002 | |
| WO | WO201016352 | | 1/2014 | |
| WO | WO2014016351 | | 1/2014 | |
| WO | WO2014016353 | | 3/2014 | |
| WO | WO2015043931 | | 2/2015 | |

OTHER PUBLICATIONS

Janusz Jachowicz et al., "Using Texture Analysis to Substantiate Hair Care Claims", Cosmetics & Toiletries Magazine, vol. 121, No. 9, Sep. 2006. (Year: 2006).*

Walter Newman et al., "A Quantitative Characterization of Combing Force", Journal of Cosmetic Science, No. 24, Dec. 9, 1973. (Year: 1973).*

Clarence Robbins, "Chapter 9—The Physical Properties of Hair Fibers", Chemical and Physical Behavior of Human Hair, 5th Edition ,2012. (Year: 2012).*

K. Abraham Vaynberg et al., "The Aquaion SLT: A Novel Device for Measuring Hair Stiffness and Lubricity", Journal of Cosmetic Science, No. 60, Mar.-Apr. 2009. (Year: 2009).*

Clarence R. Robbins; Chemical and physical behavior of human; Chemical and physical behavior of human; pp. 439-441; United States of America, 2002.

Bharat Bhushan et al.; Friction and wear studies of human hair and skin; WEAR; 2005; 1012-1021; XP002774198; vol. 259.

Search Report and Written Opinion in PCTEP2018057202; dated May 30, 2018.

Search Report and Written Opinion in EP17163597; dated Jan. 12, 2018.

Search Report and Written Opinion in EP17163626; dated Oct. 9, 2017.

* cited by examiner

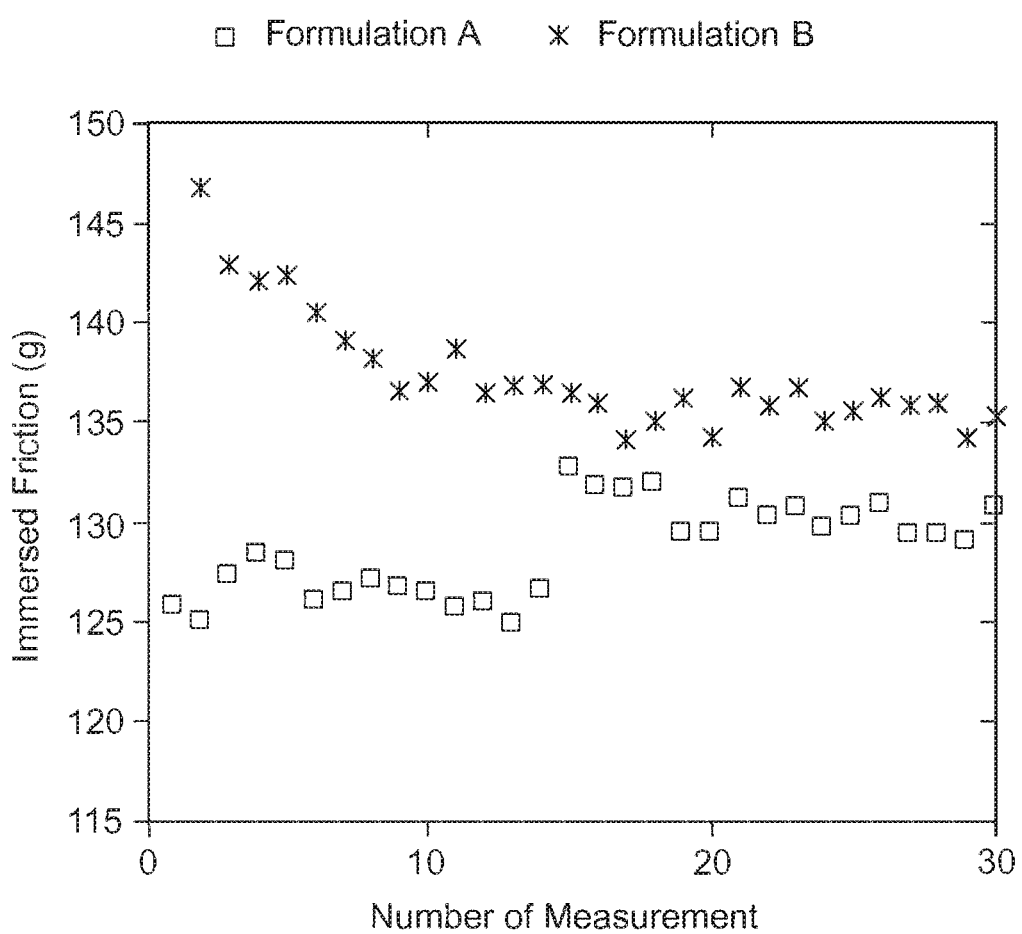

APPARATUS AND METHOD FOR MEASURING WET FRICTION OF HAIR

CROSS-REFERENCE TO RELATED APPLICATIONS

This application claims priority to International Patent Application No. PCT/EP2018/057202, filed on Mar. 21, 2018, and European Patent Application No. 17163597.2, filed on Mar. 29, 2017, both of which are incorporated herein by reference in their entireties.

TECHNICAL FIELD

The present disclosure relates to a system and method for measuring friction of wet hair, particularly relating to hair that has been treated with a hair treatment composition and to comparisons between frictions of hair treated with different treatments.

BACKGROUND

Evaluation of the friction of hair provides information about the condition of the hair, which can be affected by such things as the degree of cuticle lift, cuticle breakage, surface erosion and deposition of materials on the hair surface. It can also provide information about the efficacy of friction reducing treatments and materials. This in turn enables the beneficial choice of products that suit the particular condition of the hair.

There are a number of systems and methods available for such assessments.

Chemical and Physical Behavior of Human Hair, Clarence R. Robbins, $4^{th}$ Ed., Springer; pp 439-440, presents a summary of known techniques under the heading "Methods for Measuring Friction on Hair Fibers", including a method attributed to Scott and Robbins that involves attaching the root end of a hair fibre to the load cell of an Instron tensile tester, weighting the tip end and partially wrapping around two mandrels. The mandrels are attached to a crosshead and as they move downward against the fibre, the frictional tension is recorded. Friction is said to vary with rubbing speed, with greater differences being demonstrated between treatments at low rubbing speeds. Simulations of combing of dry hair and of hair immersed in water are disclosed using this method.

In US 20090324529, hair friction force is measured using a Texture Analyzer (TA), where a composition is applied to 10 g of hair sample. After spreading the composition on the hair sample, and before and after rinsing in water, friction force between the hair sample and a polyurethane pad is measured using the TA.

We disclose in EP1652555 the measurement of friction using a TA and a friction probe in the form of a stainless steel cylinder, coated with rubber material. A switch of hair is mounted onto the TA, the hair fibres being aligned by combing before being secured in a flat configuration. The friction probe is placed onto the hair and a load on the friction contact of approximately 560 g is applied. The probe is moved along the hair at a speed of 10 $mms^{-1}$ to measure the friction between the probe and the hair. The method is used to assess the friction properties of hair treated with different hair conditioners. However, these known methods lack the sensitivity to sufficiently differentiate between some treatments. We have found that known methods do not predict the consumer differentiation of products, particularly during the rinse stage.

We have now found that measurement of friction of a bundle of hair under water, that utilizes a friction probe that comprises surfactant on its surface enables a surprisingly sensitive measurement that correlates with consumer differentiation.

SUMMARY

In a first aspect of the present disclosure, there is provided a system for the measurement of wet friction of a bundle of hair fibres, comprising:
i) a friction probe, having a contact surface, said probe fitted with a weight in the range of from 10 to 500 g;
ii) a means for securing the bundle of hair; and
iii) a water bath;
wherein the friction probe is connected to a texture analyser; and
wherein the securing means and friction probe are positioned in the water bath below the fill line; and
wherein, the contact surface of the friction probe, comprises surfactant.

In a second aspect there is provided a method of measuring wet friction of hair, using the system of the first aspect of the present disclosure, comprising the steps of:
i) providing a bundle of hair fibres;
ii) aligning the hair fibres;
iii) securing the bundle of hair fibres;
iv) immersing the bundle of hair fibres under water in the water bath;
v) contacting the hair fibres with the contact surface of the friction probe, which is fitted with the weight;
vi) moving the probe along the hair fibres; and
vii) recording the friction generated under step vi);
wherein steps v)-vii) take place under water; and
wherein, the contact surface of the friction probe, comprises surfactant.

Preferably, steps vi)-vii) are repeated without lifting the probe from the hair, until a constant friction is obtained.

In this way, we have found that very small differences in friction are picked up, which are consistent with consumer data.

BRIEF DESCRIPTION OF THE FIGURES

Embodiments of the present disclosure will now be described with reference to the following non-limiting drawings in which:

FIG. 3 shows an immersed fiction profile for treated hair using a friction probe that comprised surfactant on its surface.

The system in FIG. 1 comprises a friction probe (1) having a contact surface (2) that comprises surfactant, fitted with a weight (3), connected to a Texture Analyser (4); and showing a bundle of hair fibres (5) clamped at two positions along its length with a clamp (6); the clamp and friction probe being positioned in a water bath (7) below the fill line (8). FIGS. 1 and 2 are referred to in the examples.

DETAILED DESCRIPTION

The Bundle of Hair Fibres

Figure 1:
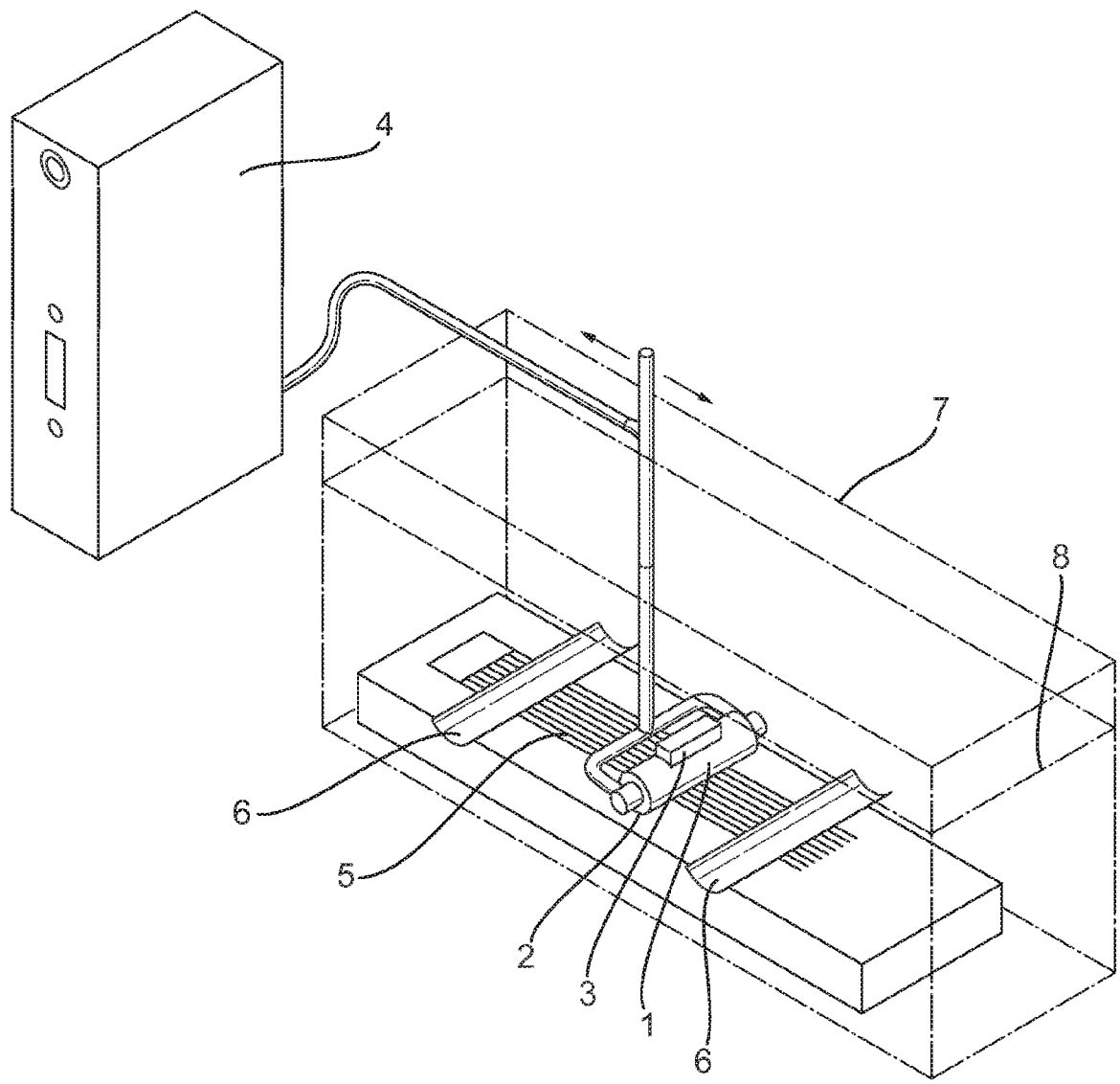
FIG. 1 is a perspective view of an example system of the present disclosure.

The bundle of hair fibres is preferably bound or glued at one end. Preferably the bundle of hair fibres is a switch preferably comprising from 50 to 5000 hair fibres, most preferably from 500 to 2000 hair fibres.

Preferably, the hair switches are from 1 to 20 g in weight, more preferably 2 to 10 g. Preferably the switches are from 10 to 50 cm in length, more preferably from 15 to 30 cm in length.

The friction probe

The friction probe has a contact surface that contacts the hair during use. The contact surface is preferably the outer surface of the friction probe. The contact surface of the friction probe comprises surfactant. Preferably the level of surfactant on the friction probe is from 10 $\mu g/cm^2$ to 1500 $\mu g/cm^2$, more preferably 50 $\mu g/cm^2$ to 1000 $\mu g/cm^2$, even more preferably 80 $\mu g/cm^2$ to 500 $\mu g/cm^2$, most preferably 100 $\mu g/cm^2$ to 200 $\mu g/cm^2$.

The weight of the friction probe itself is approximately from 20 to 100 g, preferably from 40 to 80 g, more preferably 60 g. The friction probe is fitted with a weight in the range of from 10 to 500 g, preferably from 50 to 300 g, most preferably from 100 to 200 g. The weight enables good contact between the probe and the hair.

Preferably, the friction probe comprises a rubber material, preferably a synthetic rubber, most preferably Neoprene.

Preferably, the friction probe is a stainless steel cylinder, coated with said rubber material.

Surfactant may be added to the probe by treating with aqueous surfactant and drying.

A preferred method is, prior to use, the probe is first washed with an aqueous surfactant composition, having a concentration of surfactant of from 5 to 25 wt % by weight of the total aqueous surfactant composition, and rinsed with water. The probe is then soaked in a dilute aqueous surfactant solution of concentration of from 10 ppm to 1500 ppm surfactant, and dried.

The aqueous surfactant composition, has a concentration of from 5 to 25 wt %, preferably 8 to 20 wt %, by weight of the total aqueous surfactant composition, for example, 14 wt %.

Following treatment with the aqueous surfactant composition, the probe is rinsed with water (preferably until no slippery feel remains) before being soaked in dilute aqueous surfactant solution of concentration 10 ppm to 1500 ppm, preferably 50 to 500 pm, most preferably 80 to 200 ppm, for example 140 ppm, preferably for 30 seconds to 5 minutes, more preferably from 1 minute to 3 minutes.

The probe is then dried, preferably for 10 min to 3 hours, most preferably 1.5 to 2.5 hours.

Preferably, the surfactant in both the aqueous surfactant composition and the dilute surfactant solution is an anionic surfactant, preferably Sodium Lauryl Ether Sulphate (SLES).

A preferred probe is first washed with aqueous anionic surfactant composition, having a concentration of from 5 to 25 wt %, and rinsed with water, then soaked in dilute aqueous surfactant solution of concentration of 10 ppm to 1500 ppm for 1 to 3 minutes, and dried for 1.5 to 2.5 hours.

Securing Means

The bundle of hair fibres, is secured with a securing means. Preferably, the securing means is a clamp. Preferably, the hair is secured at two positions along its length.

The Water Bath

The securing means and friction probe are positioned in the water bath below the fill line. Preferably, the water is warm, preferably between 25 and 40° C.

The Texture Analyser (TA)

Any suitable texture analyser may be used, for example, a TA. XT2i Texture Analyser supplied by Stable Micro Systems, Surrey, UK. The TA picks up the friction from the hair through the probe.

The probe is connected to the Texture Analyser.

Without wishing to be bound by any theory, it is believed that the present disclosure operates in a region between 'boundary lubrication' and 'hydrodynamic lubrication'. The region itself is normally named 'elastohydrohynamic lubrication and mixed lubrication'. In the hydrodynamic lubrication region, the fluid completely isolates the friction surfaces (the probe and the hair), and internal fluid friction alone determines tribological characteristics. In the 'boundary lubrication' region, the hydrodynamic effects of lubricants (for example, the hair composition left on the fibres), do not significantly influence tribological characteristics. By contrast, in the 'mixed lubrication' region, the fluid (such as fluid viscosity), the pressure, the solid surfaces are all influencing factors. The inventors have observed that the system according to the present disclosure can be used to differentiate even small difference of friction on hair, resulting from different hair treatment compositions. Further, the difference seems to correlate well with the consumer perception.

The Method

Preferably, steps vi)-vii) of the method are repeated without lifting the probe from the hair, until a constant friction is obtained. Preferably, steps vi)-vii) are repeated from 15 to 100 times, more preferably from 20 to 60 times, most preferably from 30 to 50 times.

Preferably, step iv)-vi) of the method are conducted without opening the security means.

The phrase 'moving the probe along the hair fibres' in Step iv) should be understood to mean that the probe is sliding on the hair fibres from one end to the other end, whilst the probe is sliding, the hair fibre is kept stationary.

The hair fibres are aligned prior to contact with the probe. This is preferably achieved by combing or brushing the hair.

A method of assessing the friction reducing efficacy of a hair treatment composition, comprises the step of treating a bundle of hair fibres with a first hair treatment composition, before carrying out the method of the first aspect of the present disclosure. Herein, 'treating' should be understood to mean applying the hair composition to a bundle of hair fibres. In a preferred embodiment, the hair fibres are cleaned and/or rinsed prior to the application of the hair composition. Preferably, the hair fibres are rinsed after application of the hair composition, but before securing it on the means.

The method may additionally comprise the step of treating a bundle of hair fibres with a second hair treatment composition, carrying out the method of the first aspect of the present disclosure and comparing the friction of hair treated with the first hair treatment composition with the friction of the hair treated with the second hair treatment composition.

The Hair Treatment Composition

Preferred hair treatment compositions for use in the methods of the invention are rinse off compositions Preferred hair treatment compositions are selected from a shampoo, a rinse-off hair conditioner and a hair mask.

Rinse off conditioners for use in the present disclosure are conditioners that are typically left on wet hair for 1 to 2 minutes before being rinsed off.

Hair masks for use in the present disclosure are treatments that are typically left on the hair for 3 to 10 minutes, preferably from 3 to 5 minutes, more preferably 4 to 5 minutes, before being rinsed off.

Treatments compositions for use in the method of the present disclosure preferably comprise conditioning agents. Conditioning agents are preferably selected from cationic surfactants, used singly or in admixture.

Cationic surfactants useful in compositions for use in the method of the present disclosure contain amino or quaternary ammonium hydrophilic moieties which are positively charged when dissolved in aqueous composition.

Examples of suitable cationic surfactants are those corresponding to the formula

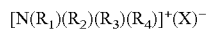

$$[N(R_1)(R_2)(R_3)(R_4)]^+(X)^-$$

in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for compositions for use in the method of the present disclosure are monoalkyl quarternary ammonium compounds in which the akyl chain lengthy is $C_{16}$ to $C_{22}$.

Suitable examples of such materials correspond to the formula:

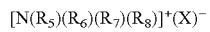

$$[N(R_5)(R_6)(R_7)(R_8)]^+(X)^-$$

in which $R_5$ is a hydrocarbon chain having 16 to 22 carbon atoms or a functionalised hydrocarbyl chain with 16 to 22 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl cahins (b) may suitably contain one or more hydrophilic moieties selected from alkoxy (preferably $C_1$-$C_3$ alkoxy), polyoxyalkylene, alkylester, and combinations thereof.

Preferably the hydrocarbon chains $R_1$ have 16 to 22 carbon atoms. They may be derived from source oils which contain substantial amounts of fatty acids having the desired hydrocarbyl chain length.

Typical monoalkyl quarternary ammonium compounds of the above general formula for use in compositions for use in the method of the present disclosure include:
(i) Cetyl trimethylammonium chloride (available commercially, for example, as Dehyquart ex BASF); behenyl trimethyl ammonium chloride (available, for example, as Incroquat™ Behenyl, ex Croda)
(ii) Compounds of the formula:

$$[N(R_1)(R_2)((CH_2CH_2O)_xH)((CH_2CH_2O)_yH]^+(X)^-$$

wherein:
x+y is an integer from 2 to 20;
$R_1$ is a hydrocarbyl chain having 16 to 22 carbon atoms and containing ether, ester, amido or amino moieties present as substituent's or as linkages in the radical chain;
$R_2$ is a $C_1$-$C_3$ alkyl group or benzyl group, preferably methyl, and
X is a salt-forming anion such as those selected from halogen, (e.g. chloride, bromide), acetate, citrate, lactate, glycolate, phosphate nitrate, sulphate, methosulphate and alkylsulphate radicals.
(iii) Compounds of the formula:

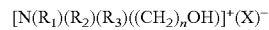

$$[N(R_1)(R_2)(R_3)((CH_2)_nOH)]^+(X)^-$$

wherein:
n is an integer from 1 to 4, preferably 2;
$R_1$ is a hydrocarbyl chain having 16 to 22 carbon atoms;
$R_2$ and $R_3$ are independently selected from $C_1$-$C_3$ alkyl groups, and are preferably methyl, and
X– is a salt-forming anion such as those selected from halogen, (e.g. chloride, bromide), acetate, citrate, lactate, glycolate, phosphate nitrate, sulphate, alkylsulphate radicals.

Mixtures of any of the foregoing cationic surfactants compounds may also be suitable.

Examples of suitable cationic surfactants for use in hair compositions for use in the method of the present disclosure include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31, Quaternium-98 and Quaternium-18. Mixtures of any of the foregoing materials may also be suitable. A particularly useful cationic surfactant is cetyltrimethylammonium chloride, available commercially, for example as DEHYQUART, ex Henkel.

The level of cationic surfactant is preferably from 0.01 to 10, more preferably 0.05 to 5, most preferably 0.1 to 2 w.t. % of the total composition.

A preferred conditioner comprises a conditioning gel phase. Such conditioners and methods for making them are described in WO2014/016354, WO2014/016353, WO2014/016352 and WO2014/016351. A preferred hair conditioning composition of this type comprises from 0.4 to 8% wt. fatty alcohol having from 8-22 carbons, from 0.1 to 2 wt % cationic surfactant component, water, and wherein the composition confers a Draw Mass of from 1 to 250 g to hair treated with the conditioning composition. Draw Mass is the mass required to draw a hair switch through a comb or brush.

The conditioning compositions may also comprise other optional ingredients. Such ingredients include, but are not limited to; fatty material, deposition polymers and further conditioning agents.

Conditioner compositions preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. The level of fatty material in conditioners is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Further conditioning ingredients include esters of fatty alcohol and fatty acids, such as cetyl palmitate.

A conditioning composition for use in the present disclosure may comprise a miscellar structured liquid.

The pH of a conditioner comprising the present composition is preferably 3-5. More preferably the pH of the composition is 4.5-5.5.

Where the composition has a pH of less than 3.10 it is preferred that it is in the form of a conditioning mask for intense treatment.

Further conditioning ingredients include conditioning oils, preferably selected from coconut oil and olive oil.

Various embodiments of the present disclosure will now be illustrated by the following non-limiting Examples:

Example 1: Compositions for Treatment of Hair Prior to Friction Analysis

Two hair conditioner compositions made by different methods were used to treat hair prior to friction analysis using the apparatus and method of the present disclosure. The compositions are given in Table 1

TABLE 1

Compositions of Conditioners A and B

| INCI | Active Level | A | B |
|---|---|---|---|
| Stearamidopropyl dimethylamine | 100 | 1 | 1.25 |
| Behentrimonium Chloride | 70 | 1 | 1.25 |
| Cetearyl Alcohol | 100 | 4 | 5 |
| Preservative | 55 | 0.1 | 0.1 |
| Sodium Chloride | 100 | 0.1 | 0.1 |
| Perfume | 100 | 0.6 | 0.6 |
| Preservative | 100 | 0.04 | 0.04 |
| Water | 100 | To 100 | To 100 |

Formulation A was made by adding the cationic surfactants to the fatty alcohol and stirring at 85° C. Gradually this mixture was added to water, typically at 55° C., such that the mixture temperature was 60° C. This temperature was maintained for 30 minutes with stirring. The mixture was then cooled towards ambient by adding more water, and other ambient temperature ingredients, and by the use of external cooling if required, and stirred.

Formulation B was made by heating the fatty alcohol and cationic surfactants in water at 75° C., and maintaining for 30 minutes with stirring. The mixture was then cooled towards ambient by adding more water, and other ambient temperature ingredients, and by the use of external cooling if required, and stirred.

Example 2: Sensory Evaluation of Wet Smooth Feel of Hair Treated with Compositions A and B 36 panelists with damaged hair used Conditioners A and B on their hair during their normal washing routines. Assessment of smoothness in the wet was made using a line scale. The results are shown in Table 2 below.

TABLE 2

Sensory smooth wet feel for hair treated with Conditioners A and B

| | A | B | Significance |
|---|---|---|---|
| No. of Panelists Conditioner in use | 36 | 36 | |
| Smooth Wet | 72.53 a | 66.09 b | 90% |

The data shows that panelists perceive that Composition A results in significantly smoother hair in the wet than Composition B, made using a different method.

Example 3: Treatment of Hair with Compositions A and B, Prior to TA Friction Measurements in Accordance with an Embodiment of the Present Disclosure The hair used was dark brown European hair, in switches of 5 g weight and 6 inch length.

The hair was treated with Compositions A and B as follows:—

Hair was first treated with a cleansing shampoo using the following method:—

The hair fibres were held under running water for 30 seconds, shampoo applied at a dose of 0.1 ml of shampoo per 1 g of hair and rubbed into the hair for 30 seconds. Excess lather was removed by holding under running water for 30 seconds and the shampoo stage repeated. The hair was rinsed under running water for 1 minute.

The wet hair was then treated with Conditioner A or B using the following method:—

Conditioner was applied to the wet hair at a dose of 0.2 ml of conditioner per 1 g of hair and massaged into the hair for 1 minute. The hair was rinsed under running water for 1 minute and excess water removed.

Example 4: Friction Measurement of Hair Treated with Compositions A and B

Friction was measured using the apparatus and method of the present disclosure as follows:

Friction was measured using a TA. XT2i Texture Analyser supplied by Stable Micro Systems, Surrey, UK. The friction probe was a stainless steel cylinder, which was coated with rubber material. In one test, the friction probe had surfactant on its outer (contact) surface and in another test, it did not.

The load on the friction contact was approximately 138 g. When in use, an area of contact between the outer surface of the friction probe and the hair of approximately 1.0 cm² was achieved.

Surfactant was Added to the Probe as Follows:

The probe was first washed with an aqueous composition of Sodium Lauryl Ether Sulphate (SLES) at a concentration of 14 wt %, by weight of the total aqueous surfactant composition, and rinsed with water. The probe was then soaked in a dilute solution of SLES having a concentration of 14 ppm, for 2 minutes, and then dried for 2 hours.

The methodology used to assess the friction properties of hair treated with Conditioners A and B was as follows:

A switch of hair was securely mounted onto the texture analyser, the hair fibres being aligned by combing before being secured in a flat configuration. The hair was immersed in the water bath. The friction probe was placed onto the hair and moved along the hair at a speed of 10 mms⁻¹ to measure the friction between the probe and the hair. The measurement was repeated 30 times.

The friction values reported below are of friction hysteresis in units of g·mm, obtained by integrating the total measured friction force over the total distance travelled by the probe, with and against cuticle.

Figure 2:
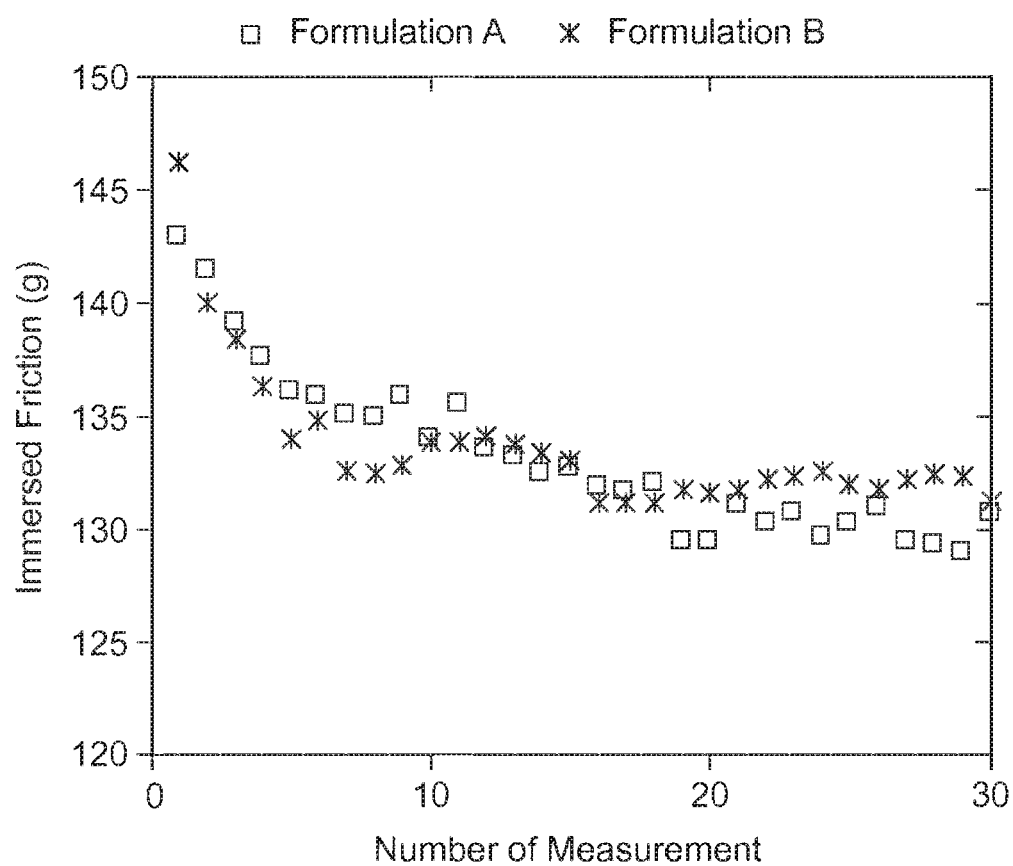
FIG. 2 shows an immersed fiction profile for treated hair using a friction probe that did not comprise surfactant on its surface.

Immersed friction measured on hair switches treated with Conditioners A and B using probes treated with surfactant or not, are given in the Table 3, and shown graphically in FIG. 2 and FIG. 3.

TABLE 3 immersed friction measurements for hair treated with Conditioners A and B when the friction probe comprised surfactant on its surface, and when the probe did not comprise surfactant on its surface.

| | Probe with surfactant | | Probe without surfactant | |
|---|---|---|---|---|
| Measurement number | Formulation A | Formulation B | Formulation A | Formulation B |
| 1 | 142.88 | 146.15 | 125.79 | 157.04 |
| 2 | 141.41 | 140.06 | 125.06 | 146.8 |
| 3 | 139.14 | 138.36 | 127.38 | 142.91 |
| 4 | 137.54 | 136.26 | 128.34 | 142.12 |
| 5 | 136.07 | 134.01 | 128.06 | 142.35 |
| 6 | 135.78 | 134.76 | 126.1 | 140.56 |
| 7 | 134.99 | 132.61 | 126.51 | 139.1 |
| 8 | 134.89 | 132.48 | 127.05 | 138.23 |
| 9 | 135.8 | 132.77 | 126.75 | 136.68 |
| 10 | 133.95 | 133.8 | 126.44 | 136.99 |
| 11 | 135.54 | 133.82 | 125.65 | 138.68 |
| 12 | 133.55 | 134.13 | 125.91 | 136.49 |
| 13 | 133.14 | 133.71 | 124.93 | 136.82 |
| 14 | 132.45 | 133.4 | 126.61 | 136.84 |
| 15 | 132.65 | 132.98 | 132.65 | 136.51 |
| 16 | 131.86 | 131.23 | 131.86 | 135.99 |
| 17 | 131.6 | 131.2 | 131.6 | 134.19 |
| 18 | 131.98 | 131.14 | 131.98 | 135.07 |
| 19 | 129.42 | 131.73 | 129.42 | 136.28 |
| 20 | 129.46 | 131.68 | 129.46 | 134.27 |
| 21 | 131.11 | 131.8 | 131.11 | 136.72 |
| 22 | 130.25 | 132.21 | 130.25 | 135.85 |
| 23 | 130.71 | 132.34 | 130.71 | 136.76 |
| 24 | 129.67 | 132.6 | 129.67 | 135.02 |
| 25 | 130.23 | 131.98 | 130.23 | 135.62 |
| 26 | 130.91 | 131.72 | 130.91 | 136.2 |
| 27 | 129.4 | 132.24 | 129.4 | 135.89 |
| 28 | 129.35 | 132.5 | 129.35 | 136 |
| 29 | 128.99 | 132.4 | 128.99 | 134.28 |
| 30 | 130.76 | 131.27 | 130.76 | 135.27 |

The data in Table 3 is presented graphically in FIGS. 2 and 3.

FIG. 2 shows the immersed fiction profile for hair treated with Conditioners A and B when the friction probe did not comprise surfactant on its surface.

FIG. 3 shows the immersed fiction profile for hair treated with Conditioners A and B when the friction probe comprises surfactant on its surface.

It will be seen that when the test probe was not pre-treated with surfactant, as shown in FIG. 2, Conditioner A and Conditioner B cannot be differentiated, unlike the corresponding sensory evaluation. However, when the probe comprising surfactant is used, the effect of the two conditioners is differentiated, and correlates with the panelist evaluation shown in Table 2 of Example 2.

Example 5: Friction Measurement by Probe Fitted with Different Weights

Composition A was used to treat the hair fibres as described in Example 1. All probes comprise surfactant prior to use. All other experimental details are as described in Example 4 except that the probe is fitted with weights of 0 g (no weight), 138 g and 1000 g respectively.

After 30 measurements, the average friction recorded for probe fitted with 138 g weight is 133.18 g mm, in good agreement with the data obtained in Table 3. The average friction recorded for probe fitted with 1000 g weight is found artificially increased to 216.22 g mm. Moreover, this high friction caused difficulty in repeating the measurements because hair constantly slipped from clamp, then floated on water. On the other hand, no weight on probe has significantly decreased the friction. No meaningful data could be recorded.

What is claimed is:

1. A system for the measurement of wet friction of a bundle of hair fibres, the system comprising:
    a friction probe having a contact surface, the friction probe fitted with a weight in the range of from 10 g to 500 g, inclusive;
    a means for securing the bundle of hair fibres; and
    a water bath;
    wherein the friction probe is connected to a texture analyser;
    wherein the means and the friction probe are positioned in the water bath below a fill line; and
    wherein the contact surface of the friction probe comprises surfactant.

2. The system of claim 1, wherein a level of the surfactant on the contact surface of the friction probe is from 10 μg/cm² to 1500 μg/cm², inclusive.

3. The system of claim 1 wherein the friction probe comprises a rubber material.

4. The system of claim 1 wherein the friction probe is first washed with an aqueous surfactant composition having a concentration of surfactant of from 5 wt % to 25 wt %, inclusive, by weight of the total aqueous surfactant composition, and rinsed with water, before being soaked in a dilute aqueous surfactant solution of concentration of from 10 ppm to 1500, inclusive, surfactant, and dried.

5. A method of measuring a wet friction of hair using a system having a friction probe positioned within a water bath and having a contact surface comprising surfactant and fitted with a weight, a means for securing a bundle of hair fibres, the means positioned within the water bath, and a texture analyser connected to the friction probe, the method comprising the steps of:
    i) providing a bundle of hair fibres;
    ii) aligning the bundle of hair fibres;
    iii) securing the bundle of hair fibres;
    iv) immersing the bundle of hair fibres under water in the water bath;

v) contacting the bundle of hair fibres with the contact surface of the friction probe;

vi) moving the friction probe along the bundle of hair fibres; and vii) recording the friction generated under step vi);

wherein steps v)-vii) take place under water.

6. The method of claim 5, wherein steps vi) to vii) are repeated from 15 times to 100 times, inclusive.

7. The method of claim 5, further comprising the step of treating the bundle of hair fibres with a first hair treatment composition.

8. The method of claim 7, further comprising the steps of:

treating the bundle of hair fibres with a second hair treatment composition; and comparing the friction of the bundle of hair fibres treated with the first hair treatment composition with the friction of the bundle of hair fibres treated with the second hair treatment composition.

9. A system comprising:

a friction probe having a contact surface with surfactant covering a portion of the contact surface, the friction probe configured to interface with hair;

a weight disposed on the friction probe; and a texture analyser communicable with the friction probe and configured to receive a friction of the hair from the friction probe.

10. The system of claim 9, further comprising:

a first clamp configured to clamp the hair against a surface; and a second clamp configured to clamp the hair against the surface;

wherein the friction probe is located between the first clamp and the second clamp.

11. The system of claim 9, further comprising a water bath defined by a fill line, the water bath containing water up to the fill line;

wherein the friction probe and the weight are located within the water bath below the fill line; and wherein the texture analyser is external to the water bath.

12. The system of claim 9, wherein a combined mass of the weight and the friction probe is between 140 g and 280 g, inclusive.

13. The system of claim 9, wherein:

the friction probe comprises a stainless steel cylinder having an exterior surface;

the exterior surface is coated with a rubber material; and the contact surface is on the exterior surface.

\* \* \* \* \*